(12) United States Patent
Herrmann et al.

(10) Patent No.: US 6,552,139 B1
(45) Date of Patent: Apr. 22, 2003

(54) PROCESS FOR PREPARING ACYCLIC OLEFINS USING HOMOBIMETALLIC AND HETEROBIMETALLIC ALKYLIDENE COMPLEXES OF RUTHENIUM CONTAINING N-HETEROCYCLIC CARBENE LIGANDS

(75) Inventors: Wolfgang Anton Herrmann, Freising (DE); Florian J. Kohl, München (DE); Thomas Weskamp, München (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/488,630

(22) Filed: Jan. 20, 2000

(30) Foreign Application Priority Data

Jan. 22, 1999 (DE) .......................................... 199 02 439

(51) Int. Cl.$^7$ .......................... C08F 4/80; C08F 132/02; C07F 9/80; C07F 15/00; C07D 249/08

(52) U.S. Cl. ....................... 526/171; 526/308; 548/103; 548/266.2; 556/136

(58) Field of Search .............................. 548/103, 266.2; 556/136; 526/171, 308

(56) References Cited

PUBLICATIONS

Wu, et al, 1995 J. Am. Chem. Soc. 117, 5503–5511.*

Weskamp, T. et al. "A novel class of ruthenium catalysts for olefin metathesis." Angew. Chem. Int. Ed. 37(18), 2490–2493 (1998).

* cited by examiner

*Primary Examiner*—Joseph K. McKane
*Assistant Examiner*—Andrea D. Small
(74) *Attorney, Agent, or Firm*—Connolly Bove Lodge & Hutz LLP

(57) ABSTRACT

The invention relates to complexes of ruthenium of the structural formula I

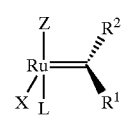

where
  X is an anionic ligand,
  Z is a monodentate to tridentate ligand which contains a metal and is nonionically bound to the ruthenium center,
  $R^1$ and $R^2$ are identical or different and are each hydrogen or/and a hydrocarbon group, but may also form a ring, and
  Ligand L is an N-heterocyclic carbene, and also to a process for preparing acyclic olefins having two or more carbon atoms or/and cyclic olefins having three or more carbon atoms and the use of at least one complex of the formula I in olefin metathesis.

10 Claims, 1 Drawing Sheet

PROCESS FOR PREPARING ACYCLIC OLEFINS USING HOMOBIMETALLIC AND HETEROBIMETALLIC ALKYLIDENE COMPLEXES OF RUTHENIUM CONTAINING N-HETEROCYCLIC CARBENE LIGANDS

BACKGROUND OF THE INVENTION

1. Field of the Invention

The invention relates to homobimetallic and heterobimetallic alkylidene complexes of ruthenium containing N-heterocyclic carbene ligands and a process for preparing olefins from acyclic olefins having two or more carbon atoms or/and from cyclic olefins having three or more carbon atoms by olefin metathesis, in which at least one of these bimetallic alkylidene complexes is used as catalyst.

2. Description of the Prior Art

Transition metal-catalyzed formation of C—C bonds is among the most important reactions of organic synthetic chemistry. Olefin metathesis is an important example of such a reaction since it enables olefins free of by-products to be synthesized. Olefin metathesis has not only a high potential in the field of preparative, organic synthesis, e.g. for ring-closure metathesis (RCM), ethenolysis or the metathesis of acyclic olefins, but also in polymer chemistry, e.g. for ring-opening metathesis polymerization (ROMP), acyclic diene metathesis (ADMET) or alkyne polymerization.

Since its discovery in the 1950s, a number of industrial processes have been able to be realized. Nevertheless, olefin metathesis has advanced to provide a broadly applicable synthetic method only in recent times as a result of the development of new catalysts (for a review article, see: J. C. Mol in: B. Comils, W. A. Herrmann, Applied Homogeneous Catalysis with Organometallic Compounds, VCH, Weinheim, 1996, p.318–332; M. Schuster, S. Blechert, Angew. Chem. 1997, 109, 2124–2144; Angew. Chem. Int. Ed. Engl. 1997, 36, 2036–2056; R. H. Grubbs, S. Chang, Tetrahedron 1998, 54, 4413–4450).

Numerous, fundamental studies have contributed significantly to an understanding of this transition metal-catalyzed reaction in which an exchange of alkylidene units between olefins occurs. The generally accepted mechanism involves metal-alkylidene complexes as active species. These react with olefins to form metallacyclobutane intermediates which undergo cycloreversion to again generate olefins and alkylidene complexes. The isolation of metathesis-active alkylidene and metallacyclobutane complexes supports these mechanistic hypotheses.

Numerous examples are found, in particular, in the complex chemistry of molybdenum and tungsten. The work of Schrock, in particular, has revealed well-defined alkylidene complexes whose reactivity can be controlled (J. S. Murdzek, R. R. Schrock, Organometallics 1987, 6, 1373–1374). The introduction of a chiral ligand sphere into these complexes makes it possible to synthesize polymers having a high tacticity (K. M. Totland, T. J. Boyd, G. C. Lavoie, W. M. Davis, R. R. Schrock, Macromolecules 1996, 29, 6114–6125). Chiral complexes of the same structural type have also been used successfully in ring-closure metathesis (O. Fujimura, F. J. d. l. Mata, R. H. Grubbs, Organometallics 1996, 15, 1865–1871; J. B. Alexander, D. S. La, D. R. Cefalo, A. H. Hoveyda, R. R. Schrock, J. Am. Chem. Soc. 1998, 120, 4041–4042). However, the high sensitivity to functional groups, air and water is a disadvantage.

Recently, phosphine-containing complexes of ruthenium have become established (R. H. Grubbs, S. T. Nguyen, L. K. Johnson, M. A. Hillmyer, G. C. Fu, WO 96/04289, 1994; P. Schwab, M. B. France, J. W. Ziller, R. H. Grubbs, Angew. Chem., 1995, 107, 2179–2181; Angew. Chem. Int. Ed. Engl. 1995, 34, 2039–2041; R. H. Grubbs, E. L. Dias, Organometallics, 1998, 17, 2758). Owing to the electron-rich, "soft" character of the later transition metals, these complexes have a high tolerance toward hard functional groups. This is demonstrated, for example, by their use in natural product chemistry (RCM of dienes) (Z. Yang, Y. He, D. Vourloumis, H. Vallberg, K. C. Nicolaou, Angew. Chem. 1997, 109, 170–172; Angew. Chem., Int. Ed. Engl. 1997, 36, 166–168; D. Meng, P. Bertinato, A. Balog, D. S. Su, T. Kamenecka, E. J. Sorensen, S. J. Danishefsky, J. Am. Chem. Soc. 1997, 119, 2733–2734; D. Schinzer, A. Limberg, A. Bauer, O. M. Böhm, M. Cordes, Angew. Chem. 1997, 109, 543–544; Angew. Chem., Int. Ed. Engl. 1997, 36, 523–524; A. Fürstner, K. Langemann, J. Am. Chem. Soc. 1997, 119, 9130–9136).

However, the opportunities for varying the phospine ligands used are greatly limited due to steric and electronic factors. Only strongly basic, bulky alkylphosphines such as tricyclohexylphosphine, triisopropylphosphine and tricyclopentylphosphine are suitable for the metathesis of acyclic olefins and relatively unstrained ring systems. Accordingly, the reactivity of these catalysts cannot be adjusted. Furthermore, chiral complexes of this structural type cannot be obtained.

It has already been able to be shown by the inventors of the present invention that the introduction of N-heterocyclic carbenes as ligands not only enables the activity of these systems to be increased but also makes it possible to achieve novel control possibilities, e.g. in respect of chirality, tacticity or regulation of the activity, owing to the significantly more variable ligand sphere (T. Weskamp, W. C. Schattenmann, M. Spiegler, W. A. Herrmann, Angew. Chem. 1998, 110, 2631–2633; Angew. Chem. Int. Ed. Engl. 1998, 37, 2490–2493).

However, even when they have tolerance toward functional groups, all ruthenium systems still have an activity which is significantly less than that of molybdenum and tungsten.

For these reasons, it is an object of the invention to develop tailored metathesis catalysts which have not only a high tolerance toward functional groups and a more variable ligand sphere but also significantly increased activities.

SUMMARY OF THE INVENTION

This object is achieved according to the invention by a complex of ruthenium having the structural formula I,

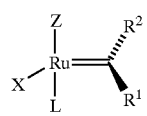

where X is an anionic ligand,

Z is a monodentate to tridentate ligand which contains a metal and is nonionically bound to the ruthenium center, $R^1$ and $R^2$ are identical or different and can also form a ring, $R^1$ and $R^2$ are each hydrogen or/and a hydrocarbon group, where the hydrocarbon groups can be identical or different and each be a straight-chain or branched or/and cyclic radical selected from the group consisting of alkyl radicals having from 1 to 50 carbon atoms, alkenyl radicals having from 2 to 50 carbon atoms, alkynyl radicals having from 2 to 50 carbon atoms, aryl radicals having from 6 to 30 carbon atoms and silyl radicals, where one or more of the hydrogen atoms in the hydrocarbon or/and silyl groups may be replaced by identical or independently different alkyl, aryl, alkenyl, alkynyl, metallocenyl, halogen, nitro, nitroso, hydroxy, alkoxy, aryloxy, amino, amido, carboxyl, carbonyl, thio or/and sulfonyl groups, the ligand L is an N-heterocyclic carbene having one of the formulae II–V,

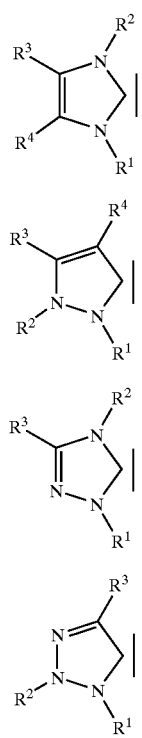

where $R^1$, $R^2$, $R^3$ and $R^4$ in the formulae II, III, IV and V are identical or different and are each hydrogen or/and a hydrocarbon group, where the hydrocarbon groups are identical or different and are independently cyclic, straight-chain or/and branched radicals selected from the group consisting of alkyl radicals having from 1 to 50 carbon atoms, alkenyl radicals having from 2 to 50 carbon atoms, alkynyl radicals having from 2 to 50 carbon atoms, aryl radicals having from 6 to 30 carbon atoms, in which at least one hydrogen may be replaced by a functional group and where $R^3$ and $R^4$ may be identical or different and may each independently be a halogen, nitro, nitroso, alkoxy, aryloxy, amido, carboxyl, carbonyl, thio, silyl or/and sulfonyl group.

DETAILED DESCRIPTION OF THE INVENTION

Figure 1:
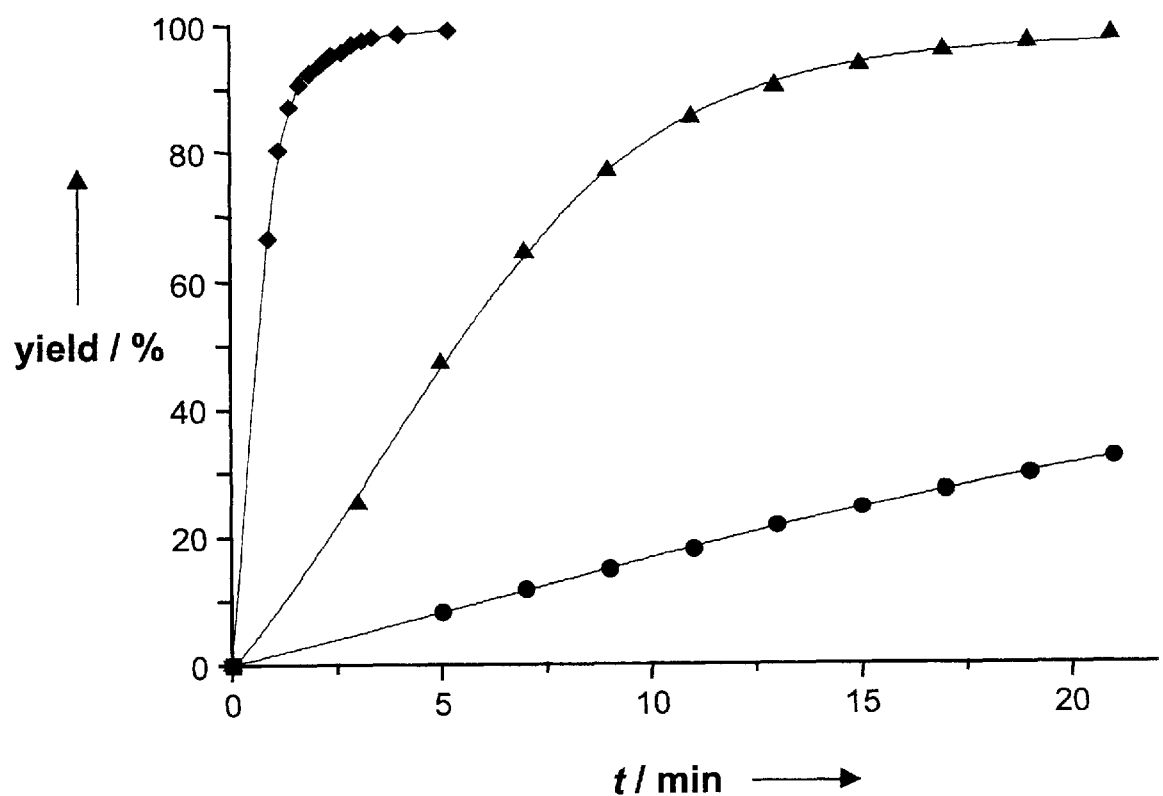
FIG. 1 is a graphic depiction of the percentage yield over time of the ring opening metathesis polymerization of 1,5-cyclooctadiene using as catalysts the following: ♦ complex 3 from the examples; ▼ complex 1 from the examples; and ● $RuCl_2(PCy_3)_2(CHPh)$.

The alkylidene complexes having the structure according to the invention and containing an N-heterocyclic carbene ligand in combination with a bidentate to tridentate ligand Z are highly active catalysts for olefin metathesis. They are particularly inexpensive. Olefin metathesis using the catalysts according to the invention displays not only a high tolerance toward a wide variety of functional groups and many possibilities for variation of the ligand sphere but also, in particular, a high activity.

Variation of the simple-to-prepare N-heterocyclic carbene ligand L enables activity and selectivity to be controlled in a targeted way and additionally allows chirality to be introduced in a simple way. Thus, in the formulae II, III, IV and V, some or all of the hydrogen in the hydrocarbon groups $R^1$, $R^2$, $R^3$ and $R^4$ can be replaced by identical or independently different halogen atoms, in particular chlorine, bromine or iodine, or/and nitro, nitroso, hydroxy, aryloxy, amino, amido, carboxyl, carbonyl, thio, sulfonyl, or/and metallocenyl groups.

Examples of functional groups as substituted groups $R^1$, $R^2$, $R^3$ and $R^4$ are hydroxymethyl, 2-hydroxyethyl, 3-hydroxypropyl, aminomethyl, 2-aminoethyl, 3-aminopropyl, 2-acetylethylaminoethyl, ethoxyethyl, polyether, ethoxyacetyl, methoxycarbonylethyl, ethoxycarbonylethyl, potassium carboxylatomethyl and isopropylaminocarbonylmethy.

$R^1$ and $R^2$ can, for example, be selected from among the radicals methyl, ethyl, isopropyl, cyclopropyl, cyclohexyl, 1-phenylethyl, 1-naphthylethyl, 1-tert-butylethyl, tert-butyl, phenyl, which may be substituted by nitro, amino, hydroxy or/and carboxyl groups, mesityl, tolyl and naphthyl. If they are chiral, the radicals can also be present in (R) and (S) forms.

Examples of $R^3$ and $R^4$ are hydrogen, methyl, ethyl and phenyl, if desired substituted by a nitro, amino, hydroxy or/and carboxyl group. In these formulae $R^3$ and $R^4$ can also form a fused-on ring system.

The ligands L of the formulae II, III, IV or/and V can have central, axial or/and planar chirality.

In the formula I, Z is a monodentate to tridentate ligand $L'_n M X'_m$, where n=0 to 4, m=0 to 6 and m+n≈0, L' can be identical or different and are selected from among πr-bonded, unsaturated carbocyclic hydrocarbons and uncharged electron donors, X' can be identical or different and are each an anionic ligand selected from the group consisting of halide, pseudohalide, tetraphenylborate, perhalogenated tetraphenylborate, tetrahaloborate, hexahalophosphate, hexahaloantimonate, trihalomethanesulfonate, alkoxide, thiolate, carboxylate, tetrahaloaluminate, tetracarbonylcobaltate, hexahaloferrate (III), tetrahaloferrate(III) or/and tetrahalopalladate(II) and M is a metal.

Preferred examples of L' are cyclopentadienyl, pentamethylcyclopentadienyl or otherwise substituted cyclopentadienyl radicals, benzene and substituted benzenes, for example cymene, and also phosphines, phosphites, amines, imines, nitriles, N-heterocyclic carbenes and carbonyl.

Preferred examples of X' are halide, in particular chloride, bromide or iodide, pseudohalide, alkoxide, thiolate, amide and carboxylate. If the halid is a substituent in one of the abovementioned compounds, chloride is preferred.

The metal M can be selected from among the metals of transition groups I to VIII and main groups I to IV, in particular the metals of transition groups I, II, VI, VII and VIII and main groups I to IV, with particular preference being given to the metals of transition group VIII. Preferred examples are Os, Ru, Ir, Rh, Fe and Pd for transition group VIII, Re for transition group VII, Mo and W for transition group VI and B, Al and Si for main groups III and IV.

The anionic ligand X in the complex of the invention is preferably a halide, pseudohalide, tetraphenylborate, perhalogenated tetraphenylborate, tetrahaloborate, hexahalophosphate, hexahaloantimonate, trihalomethanesulfonate, alkoxide, phenoxide, thiolate, carboxylate, tetrahaloaluminate, tetracarbonylcobaltate, hexahaloferrate(III), tetrahaloferrate(III) or/and tetrahalopalladate(II), with halide, pseudohalide, tetraphenylborate, perfluorinated tetraphenylborate, tetrafluoroborate, hexafluorophosphate, hexafluoroantimonate, trifluoromethanesulfonate, alkoxide, phenoxide, carboxylate, tetrachloroaluminate, tertracarbonylcobaltate, hexafluoroferrate(III), tetrachloroferrate(III) or/and tetrachloropalladate(II) being preferred. Among the pseudohalides, preference is given to cyanide, thiocyanate, cyanate, isocyanate and isothiocyanate and among the halides preference is given to using chloride, bromide or iodide.

The alkyl radicals, alkenyl radicals, alkynyl radicals or alkylene radicals, alkenylene radicals, alkynylene radicals in the formulae I to VI preferably have 1 or from 2 to 20 carbon atoms, particularly preferably 1 or from 2 to 12 carbon atoms.

In the structural formula I of the complex, $R^1$ to $R^2$ are preferably hydrogen, substituted or/and unsubstituted alkyl, alkenyl or/and aryl radicals, X is preferably a halide, alkoxide or/and carboxylate ion and L is preferably an N-heterocyclic carbene of the formula II.

The complexes are usually synthesized by ligand replacement in corresponding phosphine complexes. These can, corresponding to the reaction equation, be selectively monosubstituted or else disubstituted in a first step and subsequently react, for example, with the appropriate dimer of Z in a second step to give the complex of the invention:

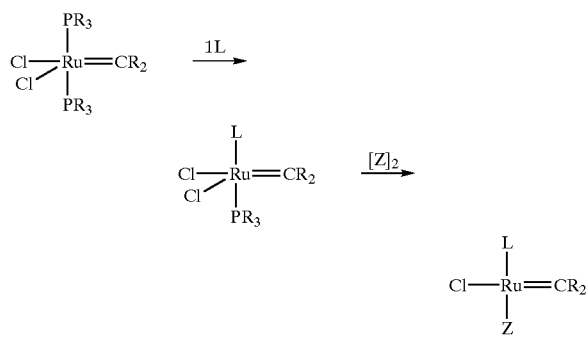

The complexes of the invention are found to be extremely efficient catalysts in olefin metathesis. The excellent metathesis activity is demonstrated by a number of examples of various metathesis reactions in the Examples.

The present invention therefore also encompasses the processes of all olefin metathesis reactions such as ring-opening metathesis polymerization (ROMP), metathesis of acyclic olefins, ethanolysis, ring-closure metathesis (RCM), acyclic diene metathesis polymerization (ADMET) and depolymerization of olefinic polymers. The high stability and tolerance of the complexes of the invention toward functional groups, in particular groups of alcohols, amines, thiols, ketones, aldehydes, carboxylic acids, esters, amides, ethers, silanes, sulfides and halogens permits the presence of such functional groups during the metathesis reaction.

The object of the invention is also achieved by a process for preparing acyclic olefins having two or more carbon atoms or/and cyclic olefins having three or more carbon atoms, in each case corresponding to the formula VI

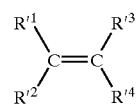

VI from acyclic olefins having two or more carbon atoms or/and from cyclic olefins having three or more carbon atoms, in each case corresponding to the formula VII, by olefin metathesis reaction in the presence of at least one of the above-described complexes, where $R^1$, $R^2$, $R^3$ and $R^4$ in the formula VI are hydrogen or/and hydrocarbon groups, where the hydrocarbon groups are identical or different and are independently straight-chain, branched or/and cyclic radicals selected from the group consisting of alkyl radicals having from 1 to 50 carbon atoms, alkenyl radicals having from 2 to 50 carbon atoms, alkynyl radicals having from 2 to 50 carbon atoms, aryl radicals having from 6 to 30 carbon atoms, metallocenyl or/and silyl radicals in which, if desired, at least one hydrogen may be replaced by a functional group, and, if desired, one or more of $R'^1$, $R'^2$, $R'^3$ and $R'^4$ may be identical or different halogen, nitro, nitroso, hxdroxy, alkoxy, aryloxy, amino, amido, carboxyl, carbonyl, thio, sulfonyl or/and metallocenyl groups.

The olefins which are used or/and are to be prepared contain one or more double bonds. In particular, $R'^1$, $R'^2$, $R'^3$ and $R'^4$ in the olefins of the formula VI can in pairs form a ring.

In the olefins of the formula VI, some or all of the hydrogen in the hydrocarbon groups $R'^1$, $R'^2$, $R'^3$ and $R'^4$ can be replaced by one or more, identical or independently different halo, silyl, nitro, nitroso, hxdroxy, alkoxy, aryloxy, amino, amido, carboxyl, carbonyl, thio, sulfonyl or/and metallocenyl groups.

Examples of $R'^1$, $R'^2$, $R'^3$ and $R'^4$ and of substituents in place of hydrogen are the same as those mentioned above in relation to the formulae I to V.

The process of the invention can be carried out with or without solvent, but preferably using organic solvents. The process of the invention can be carried out with addition of a Brönsted acid, preferably HCl, HBr, HI, $HBF_4$, $HPF_6$, or/and trifluoroacetic acid, or/and with addition of a Lewis acid, preferably $BF_3$, $AlCl_3$ or/and $ZnI_2$.

Surprisingly, this makes it possible for the first time to obtain, at a high catalytic activity, a wide variety of olefins which have been individually tailored to have various properties by simple variation of the catalysis conditions or/and the catalysts, not least because the process of the invention for preparing olefins has an unexpectedly high tolerance toward functional groups.

EXAMPLES

The following examples illustrate the invention but do not restrict its scope.

1) Preparation of the Complex of the Invention
General Procedure:

1 mmol of $RuCl_2$(di-R-imidazolin-2-ylidene)$_2$(CHPh) or $RuCl_2$(di-R-imidazolin-2-ylidene)(PCy3)(CHPh) where R is any radical, is dissolved in 5 ml of $CH_2Cl_2$ and admixed with a solution of 1 mmol of $[L'MX'_2]_2$ in 5 ml of $CH_2Cl_2$. The reaction solution is stirred at room temperature (RT) for about 15 180 minutes and the solvent is subsequently removed, the complex is washed with a toluene/pentane mixture and dried for a number of hours in a high vacuum. The reactions proceed quantitatively in the times indicated.

The following compounds were prepared using the general procedure described:

Catalyst 1)

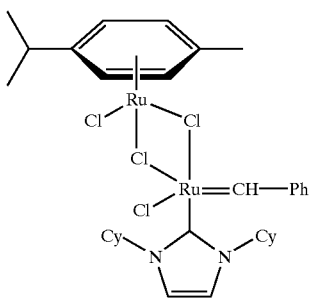

Starting materials: RuCl$_2$(di-cyclohexyl-imidazolin-2-ylidene)(PCy$_3$)(CHPh) and [(p-cymene)RuCl$_2$]$_2$;
Reaction time: 2 h;
Elemental analysis for C$_{32}$H$_{44}$Cl$_4$N$_2$Ru$_2$: calculated C, 48.00, H, 5.54, N, 3.50. found C, 48.11; H, 5.61; N, 3.52.
$^1$H NMR (CD$_2$Cl$_2$/25° C.): δ=21.14 (1H, s, Ru=CH), 7.89 (2H, d, $^3J_{HH}$=7.8 Hz, o-H of C$_6$H$_5$), 7.67 (1H, t, $^3J_{HH}$=7.8 Hz, p-H of C$_6$H$_5$), 7.22 (2H, t, $^3J_{HH}$=7.8 Hz, m-H of C$_6$H$_5$), 7.09 (1H, s, NCH), 6.65 (1H, s, NCH), 5.70 (1H, m, CH of NC$_6$H$_{11}$), 5.53, 5.50, 5.43, and 5.28 (all 1H, d, $^3J_{HH}$=5.7 Hz, CH of p-cymene) 3.05 (1H, m, CH of NC$_6$H$_{11}$), 2.85 (1H, m, CH(CH$_3$)$_2$ of p-cymene), 2.34 (3H, s, CH$_3$ of p-cymene), 1.82–0.91 (20H, all m, CH$_2$ of NC$_6$H$_{11}$), 1.41 (3H, d, $^3J_{HH}$=7.0 Hz, CH(CH$_3$)$_2$ of p-cymene), 1.27 (3H, d, $^3J_{HH}$=7.0 Hz, CH(CH$_3$)$_2$ of p-cymene). $^{13}$C NMR (CD$_2$Cl$_2$/25° C.): δ=319.4 (Ru=CH), 165.2 (NCN), 154.0 (ipso-C of C$_6$H$_5$), 131.4, 130.7, and 128.7 (o-C, m-C, and p-C of C$_6$H$_5$), 119.1 and 118.0 (NCH), 101.3, 96.8, 81.3, 80.6, 79.7, and 79.4 (p-cymene), 58.9 and 56.7 (CH of NC$_6$H$_{11}$), 36.0, 34.9, 31.3, 25.8, 25.4, and 22.3 (CH$_2$ of NC$_6$H$_{11}$), 30.8 (CH(CH$_3$)$_2$ of p-cymene), 22.2 and 21.9 (CH(CH$_3$)$_2$ of p-cymene), 18.8 (CH$_3$ of p-cymene).

Catalyst 2)

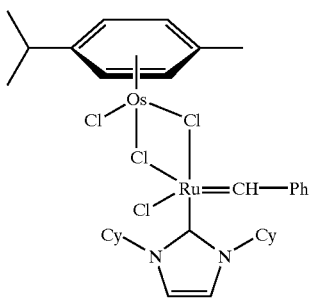

Starting materials: RuCl$_2$(di-cyclohexyl-imidazolin-2-ylidene)$_2$(CHPh) and [(p-cymene)OsCl$_2$]2;
Reaction time: 3 h;
Elemental analysis for C$_{32}$H$_{44}$Cl$_4$N$_2$OsRu: calculated C, 43.14, H, 4.98, N, 3.15. found C, 43.31; H, 5.11; N, 3.13.
$^1$H NMR (CD$_2$Cl$_2$/25° C.): δ=21.21 (1H, s, Ru=CH), 7.91 (2H, d, $^3J_{HH}$=6.4 Hz, o-H of C$_6$H$_5$), 7.72 (1H, t, $^3J_{HH}$=6.4 Hz, p-H of C$_6$H$_5$), 7.24 (2H, t, $^3J_{HH}$=6.4 Hz, m-H of C$_6$H$_5$), 7.04 (1H, s, NCH), 6.69 (1H, s, NCH), 5.70 (1H, m, CH of NC$_6$H$_{11}$), 6.08 (1H, d, $^3J_{HH}$=5.9 Hz, CH of p-cymene), 5.95 (1H, d, $^3J_{HH}$=5.9 Hz, CH of p-cymene) 5.75 (2H, app t, $^3J_{HH}$=5.9 Hz, CH of p-cymene), 3.07 (1H, m, CH of NC$_6$H$_{11}$), 2.83 (1H, m, CH(CH$_3$)$_2$ of p-cymene), 2.34 (3H, s, CH$_3$ of p-cymene), 1.90–0.85 (20H, all m, CH$_2$ of NC$_6$H$_{11}$), 1.39 (3H, d, $^3J_{HH}$=6.8 Hz, CH(CH$_3$)$_2$ of p-cymene), 1.33 (3H, d, $^3J_{HH}$=6.8 Hz, CH(CH$_3$)$_2$ of p-cymene). $^{13}$C NMR (CD$_2$Cl$_2$/25° C.): δ=319.7 (Ru=CH), 165.0 (NCN), 153.9 (ipso-C of C$_6$H$_5$), 131.2, 130.7, and 128.6 (o-C, m-C, and p-C of C$_6$H$_5$), 119.3 and 118.1 (NCH), 96.5, 91.5, 71.6, 71.4, 70.4, and 69.7 (p-cymene), 58.8 and 56.5 (CH of NC$_6$H$_{11}$), 35.8, 35.3, 31.2, 25.9, 25.2, and 22.7 (CH$_2$ of NC$_6$H$_{11}$), 31.2 (CH(CH$_3$)$_2$ of p-cymene), 22.2 and 22.1 (CH(CH$_3$)$_2$ of p-cymene), 18.7 (CH$_3$ of p-cymene).

Catalyst 3)

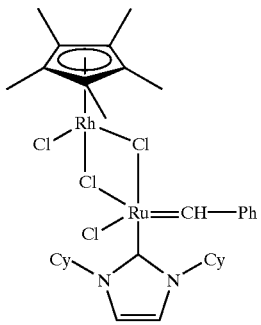

Starting materials: RuCl$_2$(di-cyclohexyl-imidazolin-2-ylidene)$_2$(CHPh) and [(Cp*RhCl$_2$]$_2$;
Reaction time: 15 min;
Elemental analysis for C$_{45}$H$_{46}$Cl$_2$N$_4$RhRu: calculated C, 47.88, H, 5.65, N, 3.49. found C, 47.99, H, 5.70, N, 3.45.
$^1$H-NMR (CD$_2$Cl$_2$/25° C.): δ=21.20 (1H, s, Ru=CH), 7.95 (2H, d, $^3J_{HH}$=7.2 Hz, o-H of C$_6$H$_5$), 7.67 (1H, t, $^3J_{HH}$=7.2 Hz, p-H of C$_6$H$_5$), 7.25 (2H, t, $^3J_{HH}$=7.8 Hz, m-H of C$_6$H$_5$), 7.09 (1H, s, NCH), 6.68 (1H, s, NCH), 6.57 (1H, m, CH of NC$_6$H$_{11}$), 2.97 (1H, m, CH of NC$_6$H$_{11}$), 1.85–0.86 (20H, all m, CH$_2$ of NC$_6$H$_{11}$), 1.74 (15H, s, CH$_3$ of Cp*). $^{13}$C NMR (CD$_2$Cl$_2$/25° C.): δ=319.3 (Ru=CH), 164.4 (NCN), 153.5 (ipso-C of C$_6$H$_5$), 131.2, 130.4, and 128.7 (o-C, m-C, and p-C of C$_6$H$_5$), 118.9 and 118.3 (NCH), 94.3 (d, J$_{RhC}$=7.5 Hz, CCH$_3$ of Cp*), 58.3 and 56.4 (CH of NC$_6$H$_{11}$), 35.2, 34.1, 33.3, 25.8, 22.4, 21.2 (CH$_2$ of NC$_6$H$_{11}$), 9.31(CH$_3$ Of CP*), 2–4) Use of the Complex of the Invention in Olefin Metathesis The examples described below demonstrate the potential of the complexes of the invention in olefin metathesis. The advantage of these novel complexes compared to known phosphine-containing systems is their significantly increased activity, particularly in ring-opening metathesis polymerization. As a result, olefins which undergo a metathesis reaction only with difficulty, if at all, can be reacted in a metathesis reaction.

2) Ring-opening Metathesis Polymerization
Norbornene, functionalized Norbornene, 1,5-cyclooctadiene and Cyclopentene serve as examples.

2a) Ring-opening Metathesis Polymerization of Norbornene

To demonstrate the activity, norbornene was subjected to a ring-opening metathesis polymerization.
Typical Reaction Batch:
In a flask, 1.0 μmol of the respective complex is dissolved in 30 ml of CH$_2$Cl$_2$. The reaction is started by addition of 20.0 mmol of norbornene and stopped after a specific time by pouring the reaction solution into 500 ml of methanol (precipitation of the polynorbornene formed). The precipitated polynorbornene is isolated by filtration and, after repeated reprecipitation from $CH_2Cl_2$/methanol or toluene/methanol, dried to constant weight in a high vacuum. The yield is determined gravimetrically.

The catalysts, reaction times, yields and turnover frequencies (TOF) are shown in Table 1.

TABLE 1

ROMP of norbornene using complexes of the invention.

| Catalyst | Monomer/catalyst | Time [s] | Yield [%] | TOF [h⁻¹] |
|---|---|---|---|---|
| 1 | 20000 | 60 | 76 | $9 \cdot 10^5$ |
| 2 | 20000 | 60 | 82 | $1 \cdot 10^6$ |
| 3 | 20000 | 20 | 80 | $3 \cdot 10^6$ |

2b) Ring-opening Metathesis Polymerization of Functionalized Norbornene derivatives.

To demonstrate the activity and the tolerance toward functional groups, 5-norbornen-2-yl acetate was subjected to a ring-opening metathesis polymerization.
Typical Reaction Batch:
In a flask, 1.0 μmol of the respective complex is dissolved in 2 ml of $CH_2Cl_2$. The reaction is started by addition of 5.0 mmol of 5-norbornen-2-yl acetate and stopped after a specific time by pouring the reaction solution into 500 ml of methanol (precipitation of the polynorbornene formed). The precipitated polynorbornene is isolated by filtration and, after repeated reprecipitation from $CH_2Cl_2$/Methanol or toluene/methanol, dried to constant weight in a high vacuum. The yield is determined gravimetrically.

The catalysts, reaction times, yields and TOFs are shown in Table 2.

TABLE 2

ROMP of 5-norbornen-2-yl acetate using complexes of the invention.

| Catalyst | Monomer/catalyst | Time [s] | Yield [%] | TOF [h⁻¹] |
|---|---|---|---|---|
| 1 | 5000 | 180 | 95 | $1 \cdot 10^5$ |
| 2 | 5000 | 180 | 95 | $1 \cdot 10^5$ |
| 3 | 5000 | 60 | 80 | $2 \cdot 10^5$ |

2c) Ring-opening Metathesis Polymerization of 1,5-Cyclooctadiene

To demonstrate the activity of the complexes of the invention, the kinetics of the ring-opening metathesis polymerization of 1,5-cyclooctadiene were monitored by NMR spectroscopy. Owing to its significantly lower ring strain compared to norbornene, 1,5-cyclooctadiene is an extremely difficult-to-polymerize substrate.
Typical Reaction Batch:
1.8 μmol of the respective complex of the invention are placed in an NMR tube and dissolved in 0.55 ml of $CD_2Cl_2$ (alternatively, a standardized solution is used). The polymerization reaction is subsequently started by addition of 55 μl of 1,5-cyclooctadiene (monomer: catalyst=250:1). The progress of the reaction is followed by recording H-NMR spectra. Integration of the time-dependent signals of product (polycyclooctadiene) and starting material (cyclooctadiene) gives the time-dependent yields of polycyclooctadiene as shown in FIG. 1 and the turnover frequencies TOF) as reported in Table 3.

TABLE 3

ROMP of 1,5-cyclooctadiene using various complexes of the invention under NMR conditions.

| Complex | Time [min] | Yield [%] | TOF [h⁻¹] |
|---|---|---|---|
| 1 | 10.9 | 80 | 1100 |
| 2 | 9.1 | 80 | 1300 |
| 3 | 1.2 | 80 | 10000 |

The TOFs achieved here are significantly above those of known systems. Thus, analogous phosphine systems, which are at the same time the most active ruthenium-based systems known from the literature, display TOFs of from 200 to a maximum of 1000 h⁻¹ under the same conditions.

2d) Ring-opening Metathesis Polymerization of Cyclopentene

Like 1,5-cyclooctadiene, cyclopentene is an extremely difficult-to-polymerize substrate.
Typical Experimental Batch:
In a flask, 1.0 μmol of the respective complex is dissolved in 1 ml of $CH_2Cl_2$. The reaction is started by addition of 5.0 mmol of cyclopentene and stopped after a specific time by pouring the reaction solution into 500 ml of methanol (precipitation of the polycyclopentene formed). The precipitated polycyclopentene is isolated by filtration and, after repeated reprecipitation from $CH_2Cl_2$/methanol or toluene/methanol, dried to constant weight in a high vacuum. The yield is determined gravimetrically. The results are summarized in Table 4.

TABLE 4

ROMP of cyclopentene using various complexes of the invention.

| Catalyst | Monomer/catalyst | Time [min] | Yield [%] | TOF [h⁻¹] |
|---|---|---|---|---|
| 1 | 5000 | 30 | 25 | 2500 |
| 2 | 5000 | 30 | 28 | 2800 |
| 3 | 5000 | 5 | 10 | 6000 |

3) Ring-closure Metathesis

The potential of the complexes of the invention in ring-closure metathesis is illustrated by the reaction of 1,7-octadiene to form cyclohexene with liberation of ethylene (Tab. 5)
Typical Reaction Batch:
A solution of 6.3 μmol of the respective complex in 2 ml of 1,2-dichloroethane was admixed with 0.45 mmol of 1,7-octadiene. After 10 minutes at 60° C., the reaction mixture was analyzed by GC/MS.

TABLE 5

RCM of 1,7-octadiene using various complexes of the invention.

| Catalyst | Monomer/catalyst | Time [min] | Yield [%] |
|---|---|---|---|
| 1 | 50 | 10 | >98 |
| 2 | 50 | 10 | >98 |
| 3 | 50 | 10 | >98 |

4) Metathesis of Acyclic Olefins

The potential of the complexes of the invention in the metathesis of acyclic olefins is illustrated by the homometathesis of 1-octene to form 7-tetradecene with liberation of ethylene (Tab. 6)

Typical Reaction Batch:

A solution of 6.0 μmol of the respective complex in 1 ml of 1,2-dichloroethane was admixed with 3.0 mmol of 1-octene. After 3 hours at 45° C., the reaction mixture was analyzed by GC/MS.

TABLE 6

Homometathesis of 1-octene using various complexes of the invention.

| Catalyst | Monomer/catalyst | Time [h] | Yield [%] | trans/cis |
|---|---|---|---|---|
| 1 | 500 | 3 | 51 | 3.7 |
| 2 | 500 | 3 | 47 | 3.4 |
| 3 | 500 | 3 | 22 | 3.5 |

ROMP of 1,5-cyclooctadiene using complexes of the invention: ♦ complex 3; ▼ complex 1; and ● $RuCl_2(PCy_3)_2(CHPh)$ (P. Schwab, M. B. France, J. W. Ziller, R. H. Grubbs, Angew. Chem., 1995, 107, 2179–2181; Angew, Chem. Int. Ed. Engl. 1995, 34, 2039–2041).

What is claimed is:

1. A process for preparing acyclic olefins having two or more carbon atoms or cyclic olefins having three or more carbon atoms, in each case corresponding to the formula VI:

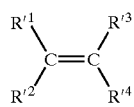

VI from acyclic olefins having two or more carbon atoms or from cyclic olefins having three or more carbon atoms, in each case corresponding to the formula VI, wherein $R'^1$, $R'^2$, $R'^3$ and $R'^4$ in the formula VI are identical or different and are each a hydrogen atom or a hydrocarbon group, where the hydrocarbon groups are identical or different and are independently straight-chain, branched or cyclic radicals selected from the group consisting of alkyl radicals having from 1 to 50 carbon atoms, alkenyl radicals having from 2 to 50 carbon atoms, alkynyl radicals having from 2 to 50 carbon atoms, aryl radicals having from 6 to 30 carbon atoms, metallocenyl and silyl radicals in which, at least one hydrogen is optionally replaced by a functional group, and one or more of $R'^1$, $R'^2$, $R'^3$ and $R'^4$ are optionally identical or different halo, nitro, nitroso, hydroxy, alkoxy, aryloxy, amino, amido, carboxyl, carbonyl, thio, sulfonyl or metallocenyl groups, or one or more pairs of $R'^1$, $R'^2$, $R'^3$ and $R'^4$ form one or more rings;

the process comprising contacting an olefin with at least one catalyst such that an olefin metathesis reaction occurs, wherein the catalyst comprises the complex of ruthenium of formula I

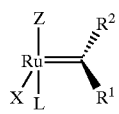

I where X is an anionic ligand,

Z is a monodentate, bidentate or tridentate ligand which contains a metal and is nonionically bound to the ruthenium center, $R^1$ and $R^2$ are identical or different and are hydrogen or a hydrocarbon group, where the hydrocarbon groups are identical or different and are each a straight-chain, branched or cyclic radical selected from the group consisting of alkyl radicals having from 1 to 50 carbon atoms, alkenyl radicals having from 2 to 50 carbon atoms, alkynyl radicals having from 2 to 50 carbon atoms, aryl radicals having from 6 to 30 carbon atoms and silyl radicals, where one or more of the hydrogen atoms in the hydrocarbon or silyl groups may be replaced by identical or independently different alkyl, aryl, alkenyl, alkynyl, metallocenyl, halogen, nitro, nitroso, hydroxy, alkoxy, aryloxy, amino, amido, carboxyl, carbonyl, thio or sulfonyl groups, or $R^1$ and $R^2$ are identical or different and form a ring, L is an N-heterocyclic carbene ligand having one of the formulas II–V:

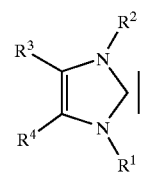

II

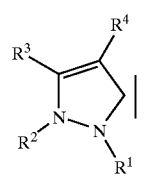

III

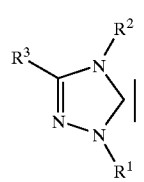

IV

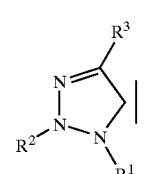

V where $R^1$, $R^2$, $R^3$ and $R^4$ in the formulas II, III, IV and V are identical or different and are each hydrogen or a hydrocarbon group, where the hydrocarbon groups are identical or different and are each independently cyclic, straight-chain or branched radicals selected from the group consisting of alkyl radicals having from 1 to 50 carbon atoms, alkenyl radicals having from 2 to 50 carbon atoms, alkynyl radicals having from 2 to 50 carbon atoms, and aryl radicals having from 6 to 30 atoms, in which at least one hydrogen may be replaced by a functional group and where $R^3$ and $R^4$ are identical or different and are each independently a halogen, nitro, nitroso, alkoxy, aryloxy, amido, carboxyl, carbonyl, thio or sulfonyl group.

2. The process as claimed in claim 1, wherein one or more double bonds are present in the olefins which are used or are to be prepared.

3. The process as claimed in claim 1, wherein a pair of $R'^1$, $R'^2$, $R'^3$ and $R'^4$ in the olefins of the formula VI form a ring.

4. The process as claimed in claim 1, where, in the olefins of the formula VI, some or all of the hydrogen in the hydrocarbon groups $R'^1$, $R'^2$, $R'^3$ and $R'^4$ are replaced by one or more, identically or independently different, halo, silyl, nitro, nitroso, hydroxy, alkoxy, aryloxy, amino, amido, carboxyl, carbonyl, thio, sulfonyl or metallocenyl groups.

5. The process as claimed in claim 1, wherein the process is carried out in a solution.

6. The process as claimed in claim 5, wherein the process is carried out in an organic solvent.

7. The process as claimed in claim 1, wherein the process is carried out with addition of a Brönsted acid.

8. The process as claimed in claim 7, wherein the Brönsted acid is HCl, HBr, Hl, $HBF_4$, $HPF_6$ or trifluoroacetic acid.

9. The process as claimed in claim 1, wherein the process is carried out with an addition of a Lewis acid.

10. The process as claimed in claim 9, wherein the Lewis acid is $BF_3$, $AlCl_3$, $ZnCl_2$, $CuCl_2$, or a mixture thereof.

* * * * *